(12) United States Patent
Athalin et al.

(10) Patent No.: US 8,040,506 B2
(45) Date of Patent: Oct. 18, 2011

(54) SPECTROMETER SENSOR COMPRISING MOVING OPTICAL MEANS AND CORRESPONDING SPECTROMETER

(75) Inventors: Han Athalin, Nantes (FR); Serge Lefrant, Nantes (FR)

(73) Assignee: Universite de Nantes, Nantes (FR)

( * ) Notice: Subject to any disclaimer, the term of this patent is extended or adjusted under 35 U.S.C. 154(b) by 547 days.

(21) Appl. No.: 11/993,585

(22) PCT Filed: Jun. 21, 2006

(86) PCT No.: PCT/EP2006/063391
§ 371 (c)(1),
(2), (4) Date: Aug. 20, 2008

(87) PCT Pub. No.: WO2006/136576
PCT Pub. Date: Dec. 28, 2006

(65) Prior Publication Data
US 2010/0079752 A1    Apr. 1, 2010

(30) Foreign Application Priority Data
Jun. 23, 2005   (FR) ..................................... 05 06373

(51) Int. Cl.
*G01J 3/28* (2006.01)
(52) U.S. Cl. ........................................................ 356/326
(58) Field of Classification Search .................... 356/326
See application file for complete search history.

(56) References Cited

U.S. PATENT DOCUMENTS

| 6,289,229 B1 | 9/2001 | Crowley ....................... 600/310 |
| 7,230,752 B2 * | 6/2007 | Hewlett et al. ................ 359/298 |
| 2001/0035952 A1 * | 11/2001 | Merklein .................... 356/239.2 |
| 2003/0135751 A1 * | 7/2003 | O'Donnell et al. ........... 713/200 |
| 2003/0169421 A1 | 9/2003 | Ehbets .......................... 356/328 |
| 2005/0036667 A1 * | 2/2005 | So et al. ........................ 382/128 |

FOREIGN PATENT DOCUMENTS
EP    1 489 405 A    12/2004

OTHER PUBLICATIONS

French Search Report from counterpart foreign Application No. FR 05/06373.
International Search Report from counterpart foreign Application No. PCT/EP2006/063391.

* cited by examiner

*Primary Examiner* — Tarifur Chowdhury
*Assistant Examiner* — Abdullahi Nur
(74) *Attorney, Agent, or Firm* — David D. Brush; Westman, Champlin & Kelly, P.A.

(57) ABSTRACT

A sensor for a spectrometer is provided, which includes at least one optical element onto which an excitation light source beam is directed and from which a target beam is emitted towards a sample to be analyzed. The at least one optical element can move, thereby enabling the direction of the target beam to be varied.

15 Claims, 3 Drawing Sheets

Fig.1
Fig.2
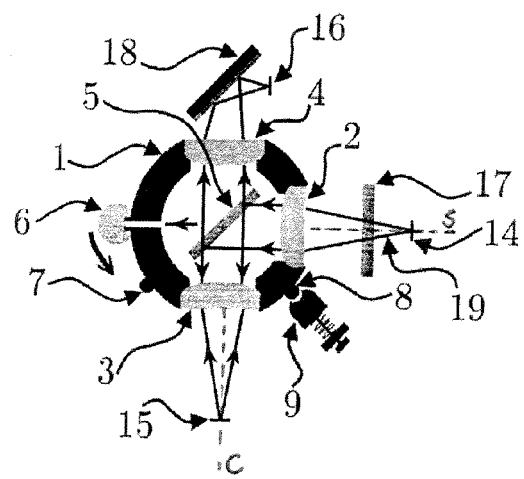
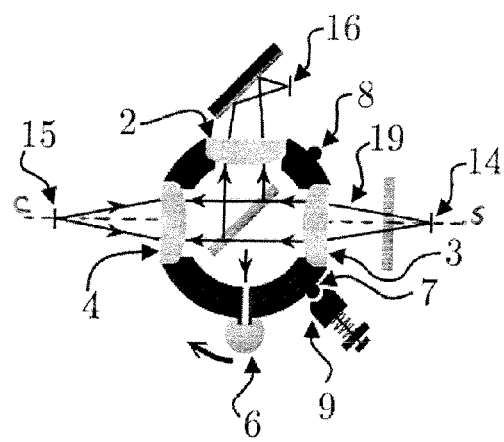
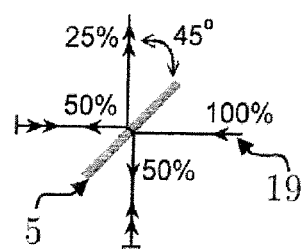
Fig.3
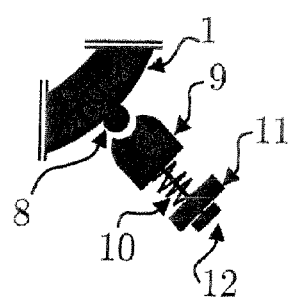
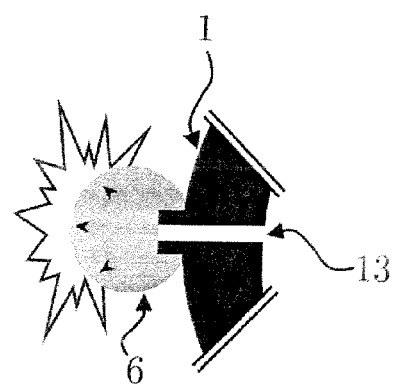
Fig.4
Fig.5

SPECTROMETER SENSOR COMPRISING MOVING OPTICAL MEANS AND CORRESPONDING SPECTROMETER

CROSS-REFERENCE TO RELATED APPLICATIONS

This Application is a Section 371 National Stage Application of International Application No. PCT/EP2006/063391, filed Jun. 21, 2006 and published as WO 2006/136576 A1 on Dec. 28, 2006, not in English.

FIELD OF THE DISCLOSURE

The field of the disclosure is that of optical analytical instrumentation. More precisely, the disclosure concerns an active sensor, for spectroscopy with complex effects and in particular Raman spectrometry and fluorescence spectrometry.

BACKGROUND OF THE DISCLOSURE

In the field of the disclosure, various types of optical fibre sensors are used for Raman spectrometry and fluorescence spectrometry.

Their common characteristic is receiving external exciting light, such as a laser beam from a spectrometer, for example by means of an optical fibre, in order to route it to the sample to be analysed. The sensor then receives the light diffused by the sample to be analysed on the same fixed focal point from where the exciting light leaves the sensor, and then returns this light diffused by the sample to the spectrometer by means of a second optical fibre.

Conventionally, the sensors comprise several optical elements, such as lenses, mirrors, filters or optical fibres.

However, at the present time, sensors are of the so-called single axis type. In other words the optical elements are fixed, which implies a single fixed point situated either perpendicular or parallel to the axis of the sensor. This limits the use of the sensors according to the location of this focal point.

In fact, under certain conditions, it is desirable to be able to modify the position of the focal point. This is possible with known sensors only by modifying the position of the sensor overall (which involves relatively long adjustment times) or by having recourse to two different sensors (which of course tends to considerably increase the cost of the device).

Moreover, each spectrometer must have its own light excitation source that is integrated in it or use an external light excitation source situated close to this spectrometer.

This proves to be fairly impractical in terms of installation.

In addition, these spectrometers are generally limited to a single wavelength for the light excitation source.

SUMMARY

An aspect of the present disclosure relates to a sensor for a spectrometer, comprising optical means on which an exciting light source beam is routed and from which a target beam is emitted towards a sample to be analysed, characterised in that said optical means are movable so as to make it possible to vary the direction of said target beam.

Thus the sensor includes a movable optical part, the arrangement of which allows, by simple change of position, the rapid and easy selection of various possible positions for the focal axis.

This makes it possible, during an analysis, to be able to change the direction of the focal point of the sensor without changing the position sensor and without changing sensor.

For example, when the space in which the analysis is to be carried out is too small to enable the sensor to be orientated in several directions, such as inside an opaque laboratory vessel or an opaque tube, the sensor makes it possible to carry out analyses in several directions.

As already mentioned, this would be possible with the sensors of the prior art, only by using two different sensors, one for example with the focal axis parallel to the axis of the sensor and the other with a focal axis perpendicular to the axis of the sensor.

According to another example, the sensor makes it possible to analyse in a narrow crucible, in a laboratory or on a hazardous site, both the residues deposited on the side walls of the crucible and the material situated at the bottom of this crucible, with a single sensor.

It will therefore be understood that an embodiment of the invention makes it possible to reduce the equipment costs in terms of analytical instrumentation hardware.

According to a preferred solution, said optical means are able to move between at least 2 positions:
 a position in which the axis of said target beam and the axis of said source beam are merged or parallel;
 a position according to which the axis of said target beam is substantially perpendicular to the axis of said source beam.

Such an arrangement makes it possible to obtain, from one and the same source beam, a bidirectional focal point, which offers possibilities corresponding to the most frequent requirements.

According to a preferential embodiment, said movable optical means comprise at least three lenses disposed so that two of said lenses have the same first focal axis, the third of said lenses having a second focal axis forming an angle of 90° with said first focal axis.

In this way a solution simple in design and easy to implement is obtained for producing a sensor with a bidirectional focal point.

Advantageously, said three lenses are carried by a rotary ring.

In this case, said optical means advantageously include a beam splitting preferably mounted inside said ring.

Thus the optical means can be integrated in the sensor while being of relatively small size.

Preferably, it comprises means of holding said movable optical means in position.

In this way, the fixity of the optical means is ensured once these are oriented in order to achieve a given focal point, which avoids any risk of loss of adjustment during analysis.

In this case, said optical means preferably comprise a movable unit associated with elastic return means that tend to press said unit against said movable optical means.

According to another characteristic, it comprises at least one indicator intended to provide an indication of the state of functioning of said source beam.

In this case, said indicator is advantageously mounted on said ring, diametrically opposite said third lens, at least one orifice being provided in said ring to allow the passage of light coming from said source beam in the direction of said indicator light.

Thus the source beam is in line with the indicator with a view to illuminating the latter effectively, and this in a very simple and therefore inexpensive fashion.

Preferably, said indicator is in the form of a piece projecting from said ring so as to form a gripping means.

The indicator thus has a dual function: one consisting of indicating the functioning of the light excitation source and one consisting of forming a gripping means for selecting the position of the focal axis.

According to another aspect of the invention, the sensor comprises a case delimiting a functional volume and includes, within said functional volume, at least one light excitation source.

Such a sensor makes it possible to envisage savings in terms of time taken to set up and use the spectrometer. This is because fitting the sensor on the spectrometer avoids having to associate therewith an external light excitation source.

In addition, if such a sensor is associated with a spectrometer that includes its own light excitation source, the sensor can give the spectrometer a new light excitation source with a different wavelength.

Preferably, said light excitation source comprises a diode laser.

According to an advantageous solution, the sensor also includes, within said functional volume, means of controlling said light excitation source.

Thus the control means are placed in the immediate vicinity of the light excitation source, which affords gains in terms of compactness of the spectrometer as well as in terms of connections.

Advantageously, the sensor also includes, within said functional volume, an energy source intended to supply said light excitation source.

Preferably, the sensor also includes, within said functional volume, ventilation means, a ventilation grill being provided in said case.

Advantageously, the sensor also includes, within said functional volume, a unit for cooling said light excitation source, said cooling unit being controlled by said control means.

In this way, the various components essential to the functioning of the light excitation source are grouped together within the sensor.

According to a preferred solution, said sensor comprises a case comprising a removable part allowing access to said functional volume delimited by said case.

It is thus possible to open the sensor easily and rapidly, with a view in particular to performing a maintenance operation inside it.

Another aspect of the invention concerns a sensor comprising optical means over which an exciting light source beam is routed and from which a target beam is emitted towards a sample to be analysed, characterised in that said optical means of said sensor are movable so as to make it possible to vary the direction of said target beam.

BRIEF DESCRIPTION OF THE DRAWINGS

Other characteristics and advantages of the invention will emerge more clearly from a reading of the following description of a preferential embodiment of the invention, given by way of illustrative and non-limitative example, and the accompanying drawings, among which:

FIGS. 1 and 2 are each a schematic view in section of a movable optical part of a sensor, respectively in a position where the focal axis is parallel to the axis of the sensor and in a position where the focal axis is perpendicular to the axis of the sensor;

FIG. 3 is a diagram explaining the separation of the exciting beam and the beam coming from the sample to be analysed when they pass through the beam splitter situated at the centre of the rotary optical part;

FIG. 4 is a schematic view in section of a self-locking unit intended to hold the movable optical means in position;

FIG. 5 is a schematic view in section of an indicator light indicating the functioning of the light excitation source

DETAILED DESCRIPTION OF ILLUSTRATIVE EMBODIMENTS

Figure 6:
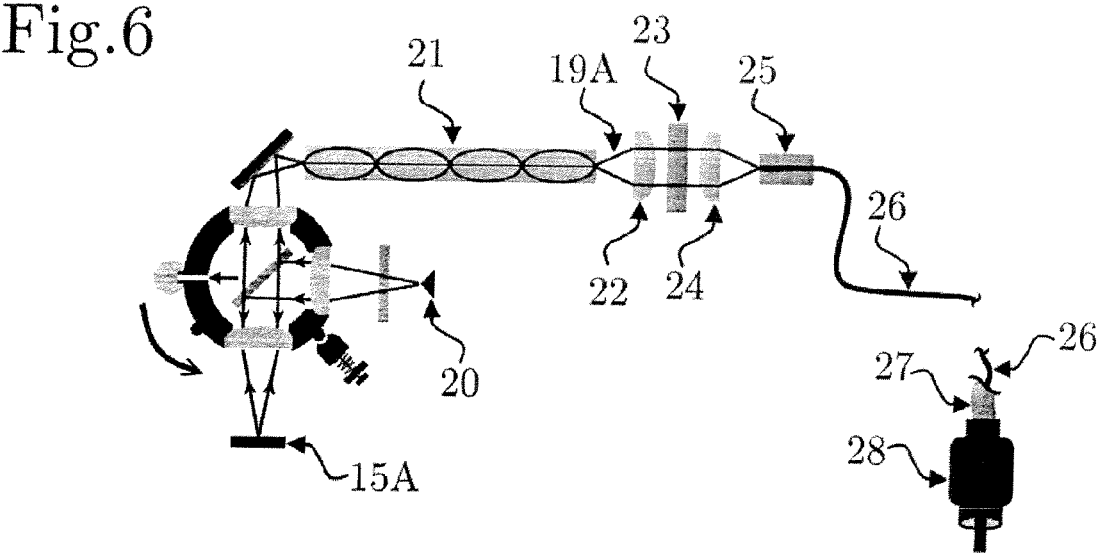
FIG. 6 is a schematic view in section of the movable optical means and of the optical fibre receiving part allowing the return of the light diffused by the sample to be analysed to the spectrometer.

As mentioned previously, the principle of an exemplary embodiment of the invention lies in equipping a sensor for a spectrometer with at least one movable optical element (herein referred to as "optical means") for varying the direction of a target beam.

FIGS. 1 and 2 illustrate a preferential embodiment of the invention according to which the optical means are able to move between two positions:

a position according to which the axis (S) of the source beam and the axis (C) of the target beam are perpendicular (FIG. 1);

a position according to which the axis (S) of the source beam and the axis (C) of the target beam are merged (FIG. 2).

The movable optical means comprise:
a ring 1 mounted so as to rotate on a fixed part of the sensor and in which three lenses 2, 3, 4 are inserted;
a beam splitter 5;
an indicator knob 6;
a self-locking unit 9.

According to the present embodiment, the three lenses 2, 3 and 4 are of the plano-convex type and are inserted in the ring 1, the lenses 3, 4 being mounted diametrically opposite on the ring 1, the lens 2 being mounted on the ring perpendicular to the lenses 3, 4.

The ring 1 is produced from a solid lightweight material such as aluminium for example, in which three cavities have been preformed for this purpose.

As it is clear, the beam splitter is mounted at the centre of the rotary ring.

In addition, an indicator knob 6, preferably spherical in shape, opaque, made from hard plastic for example, is provided so as to appear projecting at the periphery of the ring 1 so as to serve both as a handle for selecting the position of the focal axis and as an indicator light for the functioning of the light excitation source.

The "indicator light" function is fulfilled as follows.

When the light excitation source is in operation, the light that it emits passes through the orifice 13 (diametrically opposite the lens 2) and thus illuminates the indicator knob 6, as detailed in FIG. 5.

With reference to FIG. 4, the self-locking unit 9 is provided with a rod on which there are slipped a spring 10, a washer 11 fixed to the body of the sensor and a washer 12 limiting the pressure of the self-locking unit 9 on the lens system. The action of the spring tends to press the unit 9 against the stop 8 (or on the stop 7). The stops 7 and 8 hold the movable optical means in a predetermined position, that is to say, in the case shown in FIGS. 1 and 2, either with the focal axis parallel to the axis of the sensor as shown in FIG. 1 or with the focal axis perpendicular to the axis of the sensor as shown in FIG. 2.

It should be noted that the points 14, 15 and 16 are symmetrical virtual focal points coming in the case of the focal point 14 from the light excitation source and in the case of the focal point 15 from the sample to be analysed. The point 16 is an image focal point.

FIG. 3 details the separation of the source beam and the beam coming from the sample to be analysed when these beams pass through the beam splitter 5.

By way of indication, the splitter 5 is a 50:50 beam splitter.

In addition, a passband filter 17 is situated after the virtual focal point 14 in order to eliminate the stray lines and the fluorescence of the light excitation source whose beam 19 enters the movable optical means at the point 20 after having passed through the passband filter 17. A mirror 18 diverts the return light beam coming from the sample to be analysed to the optical-fibre receiving part.

The optical-fibre receiving part shown in FIG. 6 is composed of optical passive elements such as an optical guide 21, by way of example a Selfoc optical guide (registered trade mark) and two lenses 22 and 24, of the plano-convex type for example creating a finite/finite geometry and a Notch filter 23 between the two lenses 22 and 24.

The beam 19a, which comes from the sample to be analysed 15a placed at the focal point 15, is directed by the optical fibre end piece 25 inside the optical fibre 26, which sends this light beam to an external spectrometer capable of analysing the Raman effect or the fluorescence.

Figure 7:
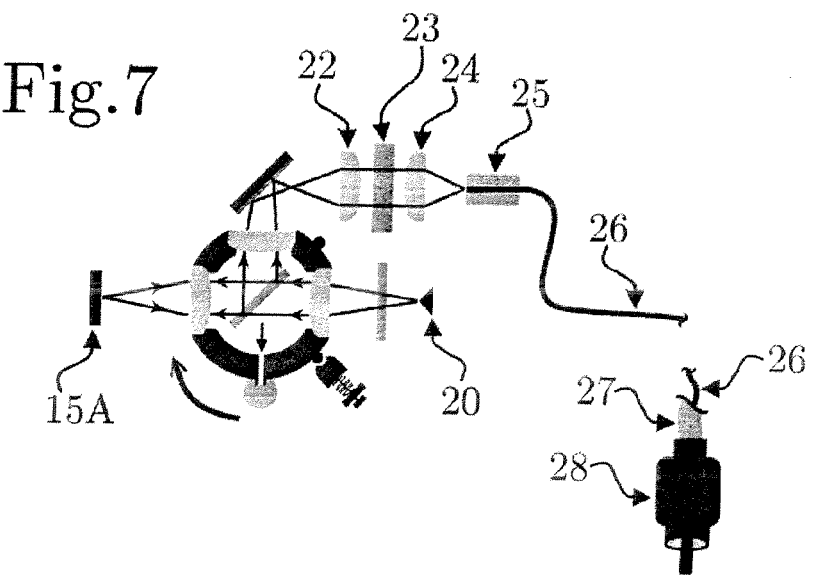
FIG. 7 is a schematic view in section of the movable optical means and of the optical fibre receiving part allowing the return of the light diffused by the sample to be analysed to the spectrometer, according to a variant embodiment.

The optical fibre 26 is protected by a sheath 27 and connected to the external spectrometer by a connector 28. The optical guide 21 serves to extend the distance between the focal point 16 and the lens 22 but can also, in another possible embodiment, be omitted, as shown in FIG. 7.

According to another aspect of the invention, the sensor comprises a case delimiting a functional volume including a light excitation source.

According to the present embodiment, the light excitation source is a diode laser 32, supplied by an energy source 35, a lithium battery for example.

The energy source is connection to a laser controller unit 33 by a connector 34. The laser controller unit 33 controls at the same time the Peltier-effect cooling unit 32A that is coupled to the diode laser 32, and to a miniature fan 39.

The miniature fan 39 is connected to the laser controller 33 by a cable 40. A ventilation grille 39A integrated in the external case of the sensor 29, allows evacuation of the heat produced by the laser to the outside of the sensor by virtue of the action of the fan 39.

The powering up and down of the light excitation source is effected by a switch 36 provided for example with a button 37 and connected to the laser controller unit 33 by a cable 38.

By way of indication, such a sensor has externally, in the form of a cylinder with a diameter of approximately 4 cm and a length of approximately 10 cm, for a weight of approximately 150 grams.

Figure 8:
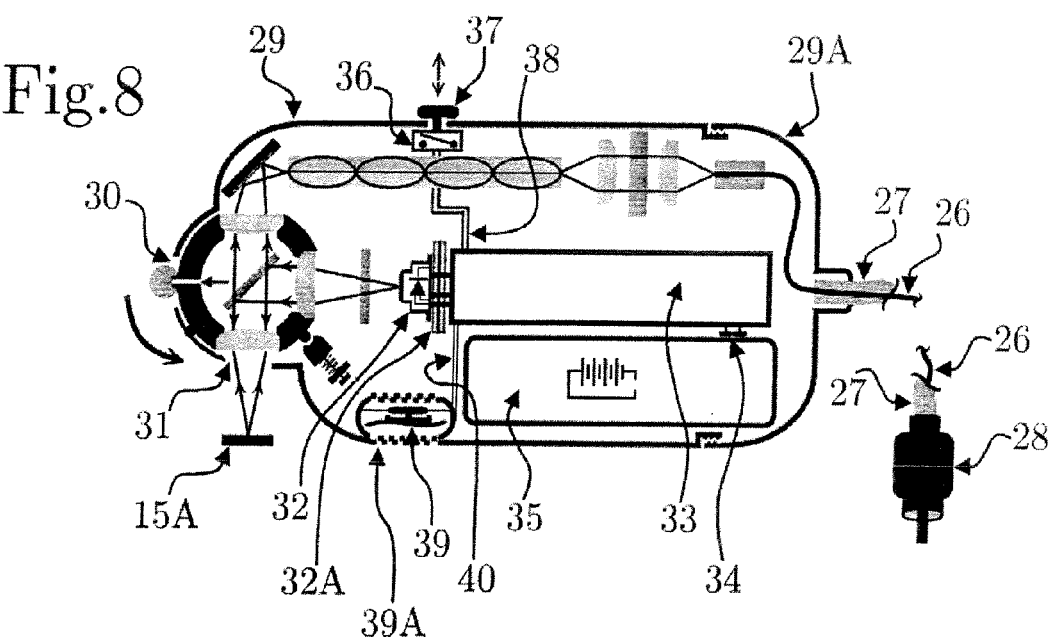
FIG. 8 is a schematic view in section of the whole of the sensor in the position where the focal axis is perpendicular to the axis of the sensor.
Figure 9:
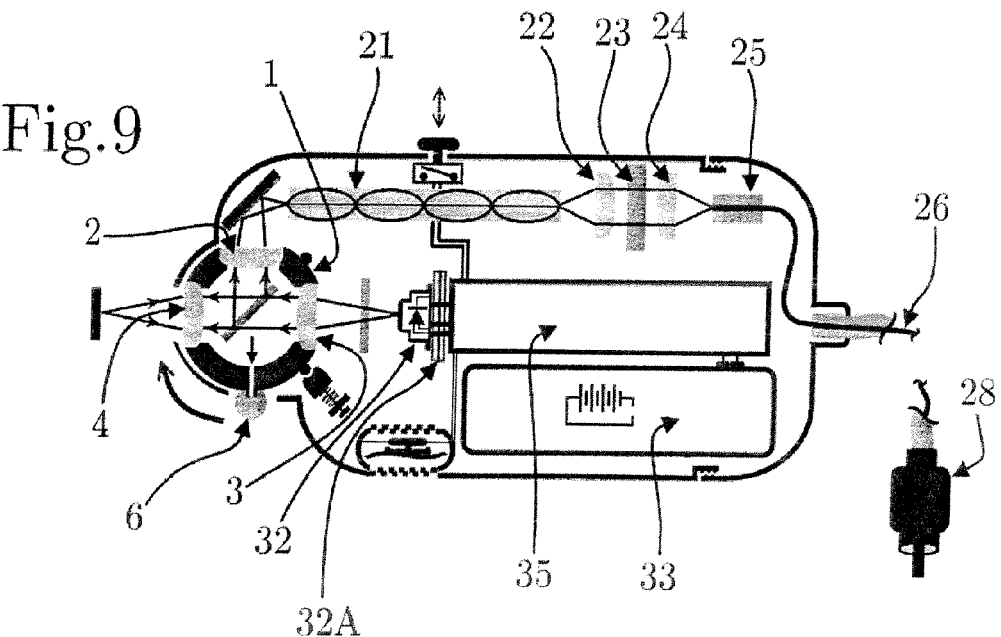
FIG. 9 is a schematic view in section of the whole of the sensor in the position where the focal axis is parallel to the axis of the sensor.

The whole of the sensor shown in FIGS. 8 and 9 is protected by an external case in two parts 29 and 29A delimiting together a functional volume.

This case is produced from a solid lightweight material such as aluminium for example, preferably cylindrical in shape. This external case is divided in two to allow the opening of the sensor in order to carry out the replacement of the energy source 35 when this is worn out or must be recharged. The removable part of the external case is the part 29A which can be screwed or fit for example on to the part 29.

The light beam coming from the light excitation source 32 leaves the sensor through the orifice 30 when the sensor is in a position where the focal axis is parallel to the axis of the sensor, or through the orifice 31 when the sensor is in a position where the focal axis is perpendicular to the axis of the sensor. These two possible positions of the focal axis are selected by the operator by means of the indicator knob 6 in order to adapt the sensor to the location of the sample to be analysed 15A.

The light excitation source can also, in another possible embodiment of the sensor, be omitted. In this case, the light excitation source part is replaced by an optical fibre that brings the light beam coming from a light excitation source external to the sensor, that of a spectrometer for example, to the rotary part of the sensor as far as the point 20. The sheath 27 then protects two optical fibres, namely the optical fibre conducting the exciting beam and the optical fibre conducting the return beam coming from the sample to be analysed.

The functioning of the sensor according to an illustrative embodiment of the invention is as follows.

When the sensor is used by an operator for analysis of a sample, an outward monochromatic light, coming from the light excitation source housed in the sensor, in this case a diode laser, passes through the passband filter, which eliminates the fluorescence and makes the beam monochromatic and narrower.

This exciting beam reaches the movable optical means of the sensor. It passes first of all through a first lens that makes it parallel and sends it to the beam splitter.

This beam splitter divides the beam, changing its axis, and sends it to a second lens that focuses it towards the outside of the sensor onto the sample to be analysed. According to the first embodiment according to which the optical means are able to move between two positions, a lens makes the exciting beam leave parallel to the axis of the sensor and the other lens makes the exciting beam leave perpendicular to the axis of the sensor.

The position of the movable optical means is selected easily and quickly by the operator by moving the indicator knob provided for this purpose to one of its two possible positions. The chosen position is fixed by means of the self-locking unit, which fits on one of the two stops situated on the rotary optical part.

The indicator knob, which is opaque, also enables the operator to check the correct functioning of the exciting light that, when it is in operation, illuminates the indicator from inside, making it luminescent.

The response of the sample to be analysed to the light excitation coming from the sensor is a return diffuse light that enters the sensor through the same lens from where the excitation light emerged. The return light reaches the light splitter, which straightens it and sends it to a lens that focuses it, and then to a mirror that reflects it on to the fibre-optic receiving part.

This fibre-optic receiving part consists of:
- an optical guide that extends the focal distance;
- the first lens that makes the beam parallel;
- a Notch filter that eliminates the Rayleigh diffusion;
- a second lens that focuses the beam in the optical fibre that will bring it as far as the spectrometer with a view to analysing it.

Naturally the invention is in no way limited to the embodiments described and depicted, which have been given only by way of non-limitative example. For example, according to another possible embodiment, the sensor may not include any light excitation source, in which case it will be necessary to use an external light excitation source, coming from a spectrometer for example, and may also not comprise an optical guide.

All the means constituting technical equivalents of the means described as well as combinations thereof if these are executed according to the spirit of the invention are included in the invention.

An exemplary embodiment of the invention proposes a sensor for a spectrometer that is not limited to a fixed focal point.

An embodiment of the invention provides such a sensor that provides the same level of reliability in terms of adjustments as the solutions of the prior art.

An embodiment of the invention provides such a sensor that makes it possible to modify the focal point by simple and rapid manipulations.

An embodiment of the invention provides such a sensor that makes it possible to optimise the ergonomics of the light spectrometers in terms of light source locations.

An embodiment of the invention provides such a sensor that reduces the equipment costs in terms of hardware.

An embodiment of the invention provides such a sensor that can be manufactured according to a compact configuration.

An embodiment of the invention provides such a sensor that is simple in design and easy to use.

Although the present disclosure has been described with reference to one or more examples, workers skilled in the art will recognize that changes may be made in form and detail without departing from the scope of the disclosure and/or the appended claims.

The invention claimed is:

1. A sensor for a spectrometer, comprising:
   at least one optical element over which an exciting light source beam is routed and from which a target beam is emitted towards a sample to be analyzed, wherein said at least one optical element is able to move so as to vary the direction of said target beam, wherein said at least one element is able to move between at least two positions, including:
   a position according to which the axis of said target beam and the axis of said source beam are merged or parallel; and
   a position according to which the axis of said target beam is substantially perpendicular to the axis of said source beam,
   wherein said movable at least one optical element comprises at least three lenses disposed so that two of said lenses have the same first focal axis, and the third of said lenses has a second focal axis forming an angle of 90° with said first focal axis,
   wherein said three lenses are carried by a rotary ring, and wherein said at least one optical element includes a beam splitter.

2. The sensor according to claim 1, wherein said beam splitter is mounted inside said ring.

3. The sensor according to claim 1, wherein the sensor comprises means for holding said movable optical element in position.

4. The sensor according to claim 3, wherein said means for holding in position comprise at least one movable unit associated with elastic return means that tend to press said unit against said movable optical element.

5. The sensor according to claim 1, wherein the sensor comprises at least one indicator configured to supply an indication of the state of functioning of said source beam.

6. The sensor according to claim 5, wherein said indicator is in the form of a piece projecting from said ring so as to form a gripping means.

7. The sensor according to claim 1, wherein said indicator is mounted on said ring, diametrically opposite said third lens, at least one orifice being provided in said ring to allow passage of light coming from said source beam in the direction of said indicator.

8. The sensor according to claim 1, comprising a case delimiting a functional volume, wherein the sensor includes, within said functional volume, at least one light excitation source.

9. The sensor according to claim 8, wherein said light excitation source comprises a diode laser.

10. The sensor according to claim 8, wherein the sensor also includes, within said functional volume, means for controlling said light excitation source.

11. The sensor according to claim 10, wherein the sensor also includes, within said functional volume, a unit for cooling said light excitation source, said cooling unit being controlled by said means for controlling.

12. The sensor according to claim 8, wherein the sensor also includes, within said functional volume, an energy source configured to supply said light excitation source.

13. The sensor according to claim 8, wherein the sensor also includes a ventilator within said functional volume and a ventilation grille in said case.

14. The sensor according to claim 1, wherein said sensor comprises a case comprising a removal part allowing access to a functional volume delimited by said case.

15. A spectrometer including:
   a sensor, comprising at least one optical element over which an exciting light source beam is routed and from which a target beam is emitted towards a sample to be analysed, wherein said at least one optical element of said sensor is movable so as to vary the direction of said target beam,
   wherein said at least one element is able to move between at least two positions:
   a position according to which the axis of said target beam and the axis of said source beam are merged or parallel; and
   a position according to which the axis of said target beam is substantially perpendicular to the axis of said source beam,
   wherein said movable at least one optical element comprises at least three lenses disposed so that two of said lenses have the same first focal axis and the third of said lenses has a second focal axis forming an angle of 90° with said first focal axis,
   wherein said three lenses are carried by a rotary ring, and wherein said at least one optical element includes a beam splitter.

* * * * *